United States Patent [19]
Thompson et al.

[11] Patent Number: 5,977,063
[45] Date of Patent: Nov. 2, 1999

[54] ALKYLATED HEXAPEPTIDES

[75] Inventors: Richard Craig Thompson, Frankfort; Stephen Charles Wilkie, Indianapolis, both of Ind.

[73] Assignee: Eli Lilly and Company, Indianapolis, Ind.

[21] Appl. No.: 09/070,371

[22] Filed: Apr. 30, 1998

Related U.S. Application Data

[60] Provisional application No. 60/047,197, May 20, 1997.

[51] Int. Cl.$^6$ .......................... A61K 38/12; A61K 38/14; C07K 9/00
[52] U.S. Cl. ...................... 514/8; 514/9; 514/11; 514/17; 530/317; 530/322; 530/329; 530/395
[58] Field of Search ................ 514/8, 9, 11, 17; 530/317, 322, 329, 395

[56] References Cited

U.S. PATENT DOCUMENTS

| | | | |
|---|---|---|---|
| 5,534,420 | 7/1996 | Debono et al. | 435/71.3 |
| 5,591,714 | 1/1997 | Nagarajan et al. | 514/9 |
| 5,721,208 | 2/1998 | Vertesy et al. | 514/9 |
| 5,763,397 | 6/1998 | Vertesy et al. | |
| 5,840,684 | 11/1998 | Cooper et al. | 514/11 |
| 5,843,889 | 12/1998 | Cooper et al. | 514/8 |

FOREIGN PATENT DOCUMENTS 0 801 075 A1   4/1997   European Pat. Off. .

OTHER PUBLICATIONS

Cooper et al., *The Journal of Antibiotics,* vol. 49, No. 6, pp. 575–581 Jun. 1996.
*J. Chem. Soc., Chem. Comm.,* Williams et al. 1694–1695 (1987).
*J. Chem Soc. Chem. Comm.,* Nagarajan, et al. 1306–1307 (1988).
*J. Antibiotics,* Pavlov, et al. vol. 46, No. 11, 1731–1739 (1993).
*J. Antibiotics,* Cristofaro, et al. vol. 48. No. 8, 805–810 (1995).
Poster at ASM Meeting, Grissom–Arnold, New Orleans, May 19–23, 1996.
*Microbial Drug Resistance,* Grissom–Arnold, 3, 53–64 (1997).
*Antibiotics Chemotherapy,* vol. 34, No. 5, 352–358 (1989).
*J. Chem Soc. Perkin. Trans. I,* Williams, 2335–2339 (1989).
*J. Antiiotics,* Miroshnikova et al, vol. 49, No. 11, 1157–1161 (1996).
*J. Natural Products,* Zmijewski, et al, vol. 52, No. 1, 203–206 (1989).
*J. Antibiotics,* Cristofarao, et al, vol. 48, No. 8, 805–810 (1995).

*Primary Examiner*—Cecilia Tsang
*Assistant Examiner*—Abdel A. Mohamed
*Attorney, Agent, or Firm*—Arlene K. Musser

[57] ABSTRACT

The present invention is directed to $N^1$-alkylated derivatives of desleucyl A82846B. These derivatives are useful as antibacterials and also as starting materials from which further antibacterial compounds are prepared.

8 Claims, No Drawings

ALKYLATED HEXAPEPTIDES

This application claims priority to provisional application Ser. No. 60/047,197 filed May 20, 1997.

BRIEF SUMMARY OF THE INVENTION

The present invention is directed to glycopeptides and is directed in particular to derivatives of desleucyl-A82846B and its $N^{DISACC}$ variations, also referred to as "hexapeptides" of A82846B. These derivatives are alkylated on the $N^1$ amine of the hexapeptide. The derivatives are useful as antibacterials.

DETAILED DESCRIPTION OF THE INVENTION

The present invention is directed to alkylated A82846B hexapeptides of the formula

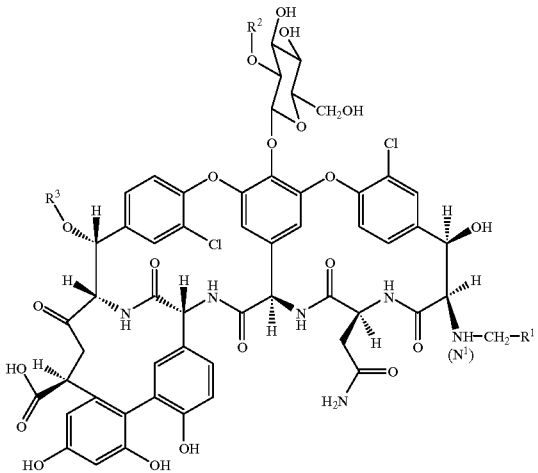

wherein $R^1$ represents
alkyl of $C_1$–$C_{11}$,
alkyl of $C_1$–$C_{11}$—$R^{1a}$, or
$R^{1a}$—(linker$_{(0 \text{ or } 1)}$)—$R^{1a}$)$_{0 \text{ or } 1}$,
wherein each $R^{1a}$ is independently phenyl or phenyl substituted by one or two substituents, each of which is independently halo, hydroxy, loweralkyl of $C_1$–$C_8$, loweralkoxy of $C_1$–$C_8$, loweralkylthio of $C_1$–$C_4$, or trifluoromethyl, and "linker" is —O—, —CH$_2$—, or —O—(CH$_2$)$_n$— wherein n is 1–3; $R^2$ represents hydrogen or an epivancosaminyl radical of the formula

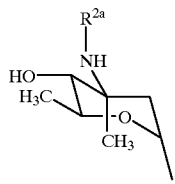

wherein $R^{2a}$ represents hydrogen or —CH$_2$—$R^1$ wherein $R^1$ is defined as above and may be the same or different than the $R^1$ on the $N^1$ position; and wherein $R^3$ represents an epivancosaminyl radical of the formula

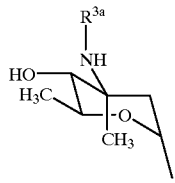

wherein $R^{3a}$ is hydrogen, or, when $R^2$ is an epivancosaminyl and $R^{2a}$ thereon is —CH$_2$—$R^1$, $R^{3a}$ can also represent —CH$_2$—$R^1$ identical to that on the $N^1$-position; and the pharmaceutically acceptable salts thereof.

The alkylated A82846B hexapeptides of the present invention are in general prepared by reductive alkylation of the corresponding A82846B hexapeptides of the formula:

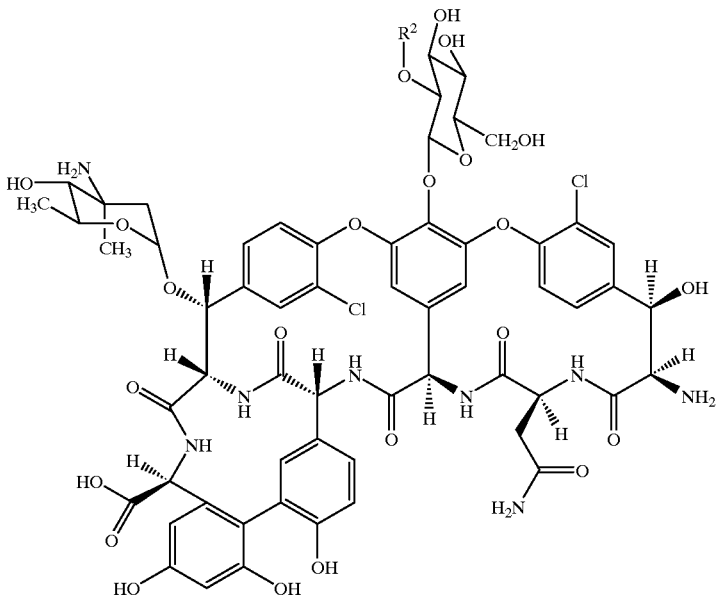

wherein $R^2$ is as defined above. In carrying out the reductive alkylation, the A82846B hexapeptide is first reacted with an aldehyde of the formula $R^1$—CHO, wherein $R^1$ is as defined above. This results in the formation of a Schiff's base, which is thereafter reduced to obtain the desired alkylated A82846B hexapeptide. Both reaction steps are carried out in a polar solvent, such as DMF, methanol, or a mixture of the same, and at temperatures of from 25° to 100° C., preferably 60° to 70° C. Preferred reducing agents are sodium borohydride and especially sodium cyanoborohydride.

In a further embodiment, the hexapeptide, aldehyde, and reducing agent, especially sodium cyanoborohydride, are all mixed together at one time. This embodiment is preferred for the reaction with nonbenzylic aldehydes, but may be used as well for the reaction with benzylic aldehydes.

Reductive alkylation of the A82846B hexapeptide can result in alkylation of more than one site. The $N^1$-position reacts preferentially, but alkylation may also occur at the $N^{DISACC}$ and/or $N^{MONOSACC}$ sites in the molecule. Different alkyl groups on the $N^1$-position and the $N^{DISACC}$ location are conveniently achieved by starting with an A82846B hexapeptide with the desired $N^{DISACC}$ group already present, and thereafter alkylating the $N^1$-position.

The starting A82846B hexapeptides are themselves synthesized from the parent glycopeptides:

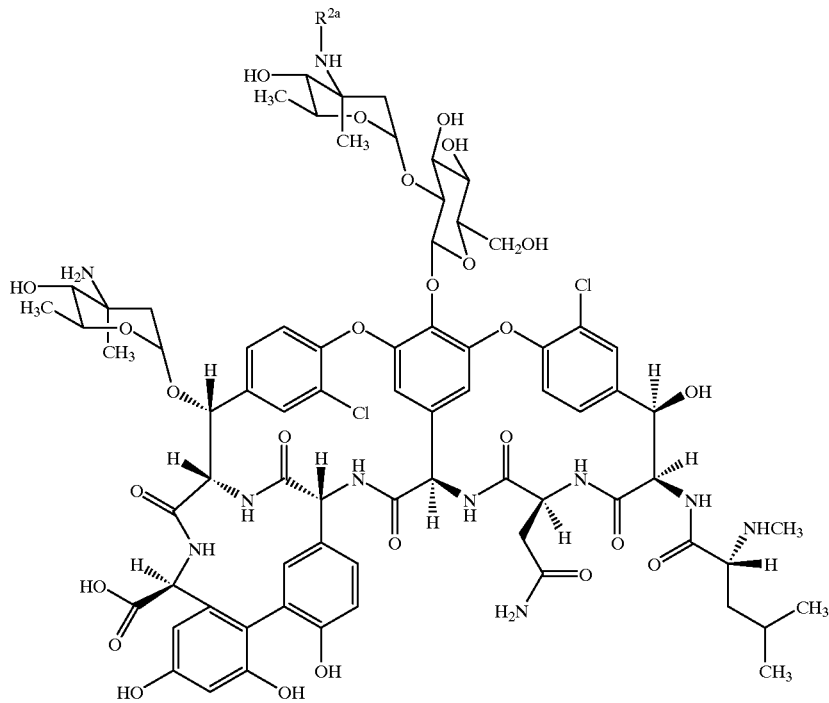

wherein $R^{2a}$ is as defined above. This synthesis is by the "Edman degradation", a two-step process for the cleavage of the N-terminal residue of a peptide or protein. In the present invention, the above parent glycopeptide is first reacted with an isothiocyanate of the formula SCN-$R^4$, to obtain an intermediate $N^{LEU}$-(thiocarbamoyl)-A82846B compound of the formula

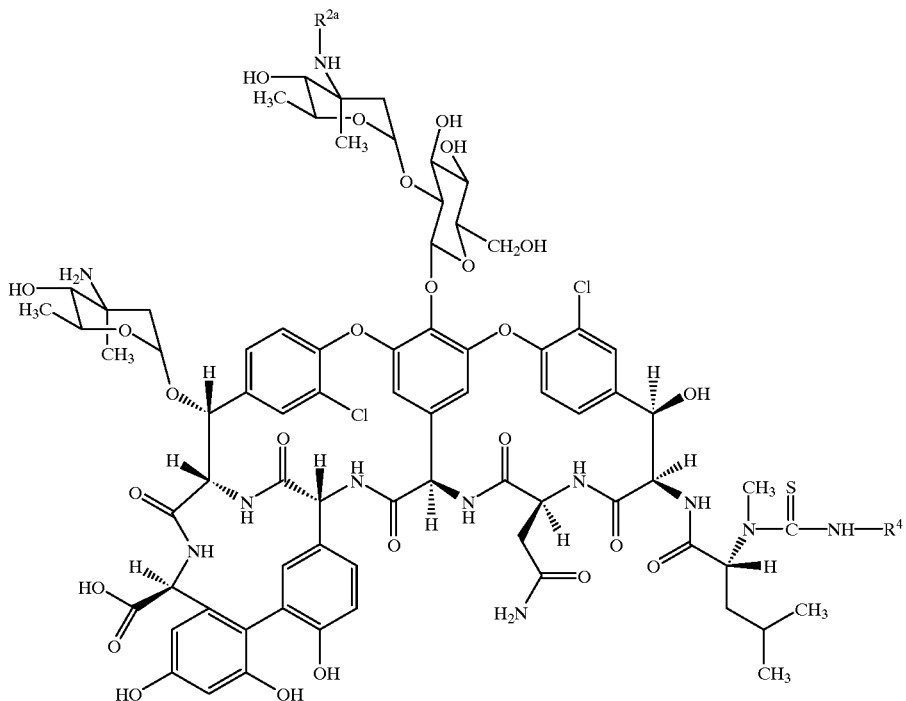

In the foregoing formula, $R^4$ represents
- alkyl of $C_1$–$C_{10}$,
- phenyl,
- naphthyl, or
- phenyl substituted by one or two substituents, each of which is independently halo, loweralkyl of $C_1$–$C_4$, loweralkoxy of $C_1$–$C_4$, benzyloxy, nitro, or

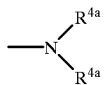

wherein each $R^{4a}$ is independently loweralkyl of $C_1$–$C_4$.

This reaction is conveniently carried out in water with pyridine, at a temperature of 25°–30° C., employing a slight excess of the isothiocyanate reactant. The $N^{LEU}$-(thiocarbamoyl)A82846B intermediate can be separated in conventional manner or can be employed after removal of reaction solvent in the second step of the Edman degradation.

In the second step, the $N^{LEU}$-(thiocarbamoyl)A82846B is reacted with an organic acid, preferably trifluoroacetic acid, in a non-polar solvent such a dichloromethane. The reaction proceeds at temperatures of from 0° C. to 35° C. but is preferably carried out at temperatures of from 0° C. to 25° C. The reaction is generally complete in several hours. The resulting hexapeptide product is separated and purified if desired in conventional procedures.

The second step of the Edman degradation can in some instances result in loss of the disaccharide epivancosamine. Longer reaction times can be used to obtain the $N^{DISACC}$-des-epivancosaminyl compound ($R^2$=hydrogen)

The compounds of the present invention readily form salts, which can be prepared in conventional manner.

The following examples illustrate the preparation of the compounds of the present invention.

Preparation of $N^{LEU}$-(phenylthiocarbamoyl)-$N^{DISACC}$-(p-(p-chlorophenyl) benzyl) A82846B $N^{DISACC}$-(p-(p-Chlorophenyl)benzyl)A82846B trihydrochloride (100.0 mg, 0.0526 mmol) was dissolved in 10 ml $H_2O$ - pyridine (1:1 v/v) and treated with phenyl isothiocyanate (0.010 ml, 0.083 mmol). The resulting mixture was stirred at room temperature for 1 hr at which time HPLC analysis indicated complete consumption of the starting material. The reaction mixture was concentrated in vacuo and the crude product was purified by preparative HPLC to give 76.6 mg (76% yield) of the title compound. FAB-MS: calc. for $C_{93}H_{102}Cl_3N_{11}O_{26}S$ 1925.5, obtained 1928.5 (M+3).

Preparation of $N^{DISACC}$-(p-(p-chlorophenyl)benzyl)-desleucyl-A82846B from Isolated Thiourea A sample of the purified $N^{LEU}$-(phenylthiocarbamoyl)-$N^{DISACC}$-(p-(p-chlorophenyl) benzyl)A82846B (63.3 mg, 0.0327 mmol) was suspended in 10 ml $CH_2Cl_2$,cooled to 0° C., then treated with trifluoroacetic acid (0.10 ml). After 1 hr the reaction mixture was warmed to room temperature and stirred an additional 2 hr. The solvent was removed in vacuo and the crude product was purified by preparative HPLC to give 25.3 mg (46% yield) of the title compound as a white powder. FAB-MS: calc. for $C_{79}H_{84}Cl_3N_9O_{25}$ 1663.5, obtained 1666.4 (M+3).

Preparation of $N^{DISACC}$-(p-phenylbenzyl)desleucyl-A82846B Without Isolation of Thiourea Intermediate $N^{DISACC}$-(p-Phenylbenzyl)A82846B (41.0 mg, 0.0233 mmol) was dissolved in 4 ml $H_2O$—pyridine (1:1 v/v) and treated with phenyl isothiocyanate (0.0040 ml, 0.033 mmol). The resulting mixture was stirred at room temperature for 3 hr at which time HPLC analysis indicated complete consumption of the starting material. The reaction mixture was concentrated in vacuo to give the crude thiourea intermediate as a white solid. The thiourea derivative was then suspended in 10 ml $CH_2Cl_2$, cooled to 0° C., then treated with trifluoroacetic acid (0.25 ml). After 30 minutes the reaction mixture was warmed to room temperature and stirred an additional 1 hr. The solvent was removed in vacuo and the crude product was purified by preparative HPLC to give 14.0 mg (37% yield) of the title compound as a white powder. FAB-MS: calc. for $C_{79}H_{85}Cl_2N_9O_{25}$ 1629.5, obtained 1632.5 (M+3).

PREPARATION OF EXAMPLE 19

A sample of purified desleucyl-A82846B (141 mg, 0.0962 mmol), 8-phenyloctanal (28 mg, 0.137 mmol), and sodium cyanoborohydride (35 mg, 0.556 mmol) were dissolved in 20 ml DMF-MeOH (1:1 v/v). The resulting mixture was heated to 65° C. and stirred for 1 hour at which time HPLC analysis revealed complete consumption of the starting material. The reaction mixture was cooled to room temperature, concentrated in vacuuo, and the crude product purified by preparative HPLC to give 20 mg (13% yield) of Example 19.

PREPARATION OF EXAMPLE 3

A sample of purified desleucyl-A82846B (140 mg, 0.0956 mmol) and 4-phenylbenzaldehyde (30 mg, 0.165 mmol) was dissolved in 20 ml DMF-MeOH (1:1 v/v). The resulting mixture was heated to 65° C. and stirred for 1.5 hours, sodium cyanoborohydride (27 mg, 0.429 mmol) was added and the reaction stirred for an additional 1.5 hours at which time HPLC analysis revealed consumption of the starting material. The reaction mixture was cooled to room temperature, concentrated in vacuo, and the crude product purified by preparative HPLC to give 38 mg (24% yield) of Example 3.

The HPLC procedures reported in these examples were as follows:

Analytical: Reactions were monitored by analytical HPLC using a Waters $C_{18}$ µBondapak or Novapak $C_{18}$ column (3.9×300 mm) and UV detection at 280 nm. Elution was accomplished with a linear gradient of 5% $CH_3CN$—95% buffer to 80% $CH_3CN$—20% buffer over 30 minutes. The buffer used was 0.5% triethylamine in water, adjusted to pH 3 with $H_3PO_4$.

Preparative: Crude reaction mixtures were purified by preparative HPLC using a Waters $C_{18}$ Nova-Pak column (40×300 mm) and UV detection at 280 nm. Elution was accomplished with a linear gradient of 5% $CH_3CN$—95% buffer to 80% $CH_3CN$—20% buffer over 30 minutes. The buffer used was 0.5% triethylamine in water, adjusted to pH 3 with $H_3PO_4$. The desired fractions were subsequently desalted with a Waters $C_{18}$ Sep-Pak (35 cc) followed by lyophilization.

Compounds were desalted as follows. A Waters Sep-Pak cartridge was pre-wet with methanol (2-3 column volumes) then conditioned with water (2-3 column volumes). The sample, dissolved in a minimum volume of water, was loaded onto the Sep-Pak column which was then washed with water (2-3 column volumes) to remove the unwanted salts. The product was then eluted with an appropriate solvent system, typically 1:1 $CH_3CN/H_2O$, $CH_3CN$, and/or methanol. The organic solvent component was removed in vacuo and the resulting aqueous solution lyophilized to give the final product.

Representative compounds of the present invention are listed in the following table:

TABLE I

| EX # | NAME | FAB-MS | M + X | Analytical HPLC*, min |
|---|---|---|---|---|
| 1 | $N^1$-(12-PHENYL-n-DODECYL)DESLEUCYL-A82846B | 1710.5 | 3 | 21.1 |
| 2 | $N^1$-(12-PHENYL-n-DODECYL)-$N^{DISACC}$-(p-PHENYLBENZYL)-DESLEUCYL-A82846B | 1876.1 | 2 | 22.9 |
| 3 | $N^1$-(p-PHENYLBENZYL)-DESLEUCYL-A82846B | 1632.5 | 3 | 14.1 |
| 4 | $N^1,N^{DISACC}$-BIS(p-PHENYLBENZYL)-DESLEUCYL-A82846B | 1798.4 | 3 | 17.4 |
| 5 | $N^1$-BENZYL-$N^{DISACC}$-(p-PHENYLBENZYL)-DESLEUCYL-A82846B | 1722.7 | 3 | 14.9 |
| 6 | $N^1,N^{MONOSACC}$-DIBENZYL-$N^{DISACC}$-(p-PHENYLBENZYL)-DESLEUCYL-A82846B | 1812.9 | 3 | 16.5 |
| 7 | $N^1,N^{DISACC}$-DIHEXYLDESLEUCYL-A82846B | 1633 | 1 | 14.2 |
| 8 | $N^1,N^{DISACC},N^{MONOSACC}$-TRI-n-HEXYLDESLEUCYL-A82846B | 1718.2 | 3 | 16.7 |
| 9 | $N^1,N^{DISACC}$-BIS(p-HYDROXYBENZYL)-DESLEUCYL-A82846B | 1679.1 | 4 | 9.9 |
| 10 | $N^1$-n-HEXYLDESLEUCYL-A82846B | 1549.6 | 2 | 11.8 |
| 11 | $N^1$-n-HEXYL-$N^{DISACC}$-(p-PHENYLBENZYL)-DESLEUCYL-A82846B | 1716.8 | 3 | 16.2 |
| 12 | $N^1$-BENZYLDESLEUCYL-A82846B | 1556.3 | 3 | 10.1 |
| 13 | $N^1$-(p-HYDROXYBENZYL)-DESLEUCYL-A82846B | 1572.1 | 3 | 9.0 |
| 14 | $N^1$-(6-PHENYL-n-HEXYL)DESLEUCYL-A82846B | 1626.1 | 3 | 15.5 |
| 15 | $N^1,N^{DISACC}$-BIS(6-PHENYL-n-HEXYL)-DESLEUCYL-A82846B | 1785.4 | 2 | 19.1 |
| 16 | $N^1,N^{DISACC}$-BIS(10 PHENYL-n-DECYL)-DESLEUCYL-A82846B | 1898.7 | 3 | 24.5 |
| 17 | $N^1$-(p-HYDROXYBENZYL)-$N^{DISACC}$-(p-PHENYLBENZYL)-DESLEUCYL-A82846B | 1737.3 | 2 | 14.1 |
| 18 | $N^1$-(10-PHENYL-n-DECYL)DESLEUCYL-A82846B | 1682.6 | 3 | 19.7 |
| 19 | $N^1$-(8-PHENYL-n-OCTYL)DESLEUCYL-A82846B | 1653.6 | 2 | 17.6 |
| 20 | $N^1$-(6-PHENYL-n-HEXYL)-$N^{DISACC}$-(p-PHENYLBENZYL)-DESLEUCYL-A82846B | 1792.5 | 3 | 18.4 |
| 21 | $N^1$-(p-(3-PHENYL-n-PROPOXY)BENZYL)DESLEUCYL-A82846B | 1690.3 | 3 | 15.9 |
| 22 | $N^1$-(p-(3,5-BIS-(TRIFLUOROMETHYL)-PHENYL)BENZYL)-DESLEUCYL-A82846B | 1768.2 | 3 | 17.5 |
| 23 | $N^1$-(p-(n-OCTYLOXY)-BENZYL)DESLEUCYL-A82846B | 1683.5 | 2 | 18.3 |
| 24 | $N^1$-(p-(METHYLTHIO)-BENZYL)DESLEUCYL-A82846B | 1602.1 | 3 | 13.6 |

TABLE I-continued

| EX # | NAME | FAB-MS | M + X | Analytical HPLC*, min |
|---|---|---|---|---|
| 25 | $N^1, N^{DISACC}$-BIS(p-(METHYLTHIO)-BENZYL)DESLEUCYL-A82846B | 1738.1 | 3 | 11.3 |
| 26 | $N^1$-(p-(3,5-BIS-(TRIFLUOROMETHYL)-PHENYL)BENZYL)-$N^{DISACC}$-(p-PHENYLBENZYL)-DESLEUCYL-A82846B | 1934.6 | 3 | 19.4 |
| 27 | $N^1$-(p-(3,5-BIS-(TRIFLUOROMETHYL)-PHENYL)BENZYL)-$N^{DISACC}$-(p-(p-CHLOROPHENYL)BENZYL-DESLEUCYL-A82846B | 1968.5 | 3 | 21.2 |
| 28 | $N^1$-(6-PHENYL-n-HEXYL)-$N^{DISACC}$-(p-(p-CHLOROPHENYL)BENZYL)DESLEUCYL-A82846B | 1826.6 | 3 | 19.3 |

*Waters $C_{18}$ μBondapak

The compounds of the present invention are useful for the treatment of bacterial infections. Therefore, in another embodiment, the present invention is directed to a method for controlling a bacterial infection in a host animal, typically a warm-blooded animal, which comprises administering to the host animal an effective, antibacterial amount of a compound of the present invention. In this embodiment, the compounds can be used to control and treat infections due to various bacteria, but especially gram-positive bacteria. In a preferred embodiment, the compounds are used to control and treat infections due to bacteria resistant to existing antibacterials. For example, certain bacteria are resistant to methicillin, and yet others are resistant to vancomycin and/or teicoplanin. The present compounds provide a technique for controlling and treating infections due to such resistant bacterial species.

In carrying out this embodiment of the invention, the compounds of the present invention can be administered by any of the conventional techniques, including the oral route and parenteral routes such as intravenous and intramuscular. The amount of compound to be employed is not critical and will vary depending on the particular compound employed, the route of administration, the severity of the infection, the interval between dosings, and other factors known to those skilled in the art. In general, a dose of from about 0.5 to about 100 mg/kg will be effective; and in many situations, lesser doses of from about 0.5 to about 50 mg/kg will be effective. A compound of the present invention can be administered in a single dose, but in the known manner of antibacterial therapy, a compound of the present invention is typically administered repeatedly over a period of time, such as a matter of days or weeks, to ensure control of the bacterial infection.

Also in accordance with known antibacterial therapy, a compound of the present invention is typically formulated for convenient delivery of the requisite dose. Therefore, in another embodiment, the present invention is directed to a pharmaceutical formulation comprising a compound of the present invention, in combination with a pharmaceutically-acceptable carrier. Such carriers are well known for both oral and parenteral routes of delivery. In general, a formulation will comprise a compound of the present invention in a concentration of from about 0.1 to about 90% by weight, and often from about 1.0 to about 3%.

The antibacterial efficacy of the present compounds is illustrated by Table II. The minimal inhibitory concentrations (MICs) were determined using a standard broth microdilution assay.

TABLE II

Antibacterial Activity, Minimal Inhibitory Concentration (MIC) against Various Organisms*

| EX # | RESISTANT | SENSITIVE | SA 446 | SA 489 | SA 447 | SH 105 | SH 415 | SE 270 | SPY C203 | SPN P1 |
|---|---|---|---|---|---|---|---|---|---|---|
| 1 | 13 | 9.2 | 8 | 2 | 2 | 4 | 8 | 4 | 0.125 | NO GROWTH |
| 2 | 45 | 24 | 32 | 64 | >64 | >64 | >64 | 32 | 4 | ≦.06 |
| 3 | >128 | 21 | 8 | 8 | 8 | 8 | 16 | 8 | ≦.06 | ≦.06 |
| 4 | 53 | 21 | 4 | 2 | 2 | 2 | 2 | 2 | ≦.06 | ≦.06 |
| 5 | 23 | 9.2 | 2 | 2 | 2 | 2 | 2 | 2 | 0.125 | 0.5 |
| 6 | 16 | 6.1 | 2 | 2 | 2 | 0.5 | 1 | 0.5 | 0.125 | 0.5 |
| 7 | >128 | 111 | 16 | 8 | 8 | 4 | 8 | 16 | 8 | 8 |
| 8 | 76 | 55 | 16 | 8 | 8 | 4 | 16 | 8 | 1 | 2 |
| 9 | >128 | >128 | 16 | 16 | 16 | 32 | 32 | 32 | 16 | 32 |
| 10 | >128 | >128 | 32 | 16 | 32 | 64 | 64 | 32 | 16 | 32 |
| 11 | 27 | 11 | 1 | 1 | 0.5 | 2 | 1 | 0.5 | 0.125 | 0.125 |
| 12 | >128 | 128 | >64 | 64 | >64 | >64 | >64 | >64 | 2 | 2 |
| 13 | 54 | 4 | 16 | 8 | 32 | >64 | >64 | 32 | 0.25 | ≦.06 |
| 14 | >50 | 37 | 16 | 8 | 8 | 8 | 8 | 8 | ≦.06 | ≦.06 |
| 15 | 8 | 6 | 4 | 2 | 2 | 1 | 2 | 2 | 0.125 | 0.5 |
| 16 | >128 | >11 | >64 | 64 | >64 | >64 | >64 | >64 | 8 | 16 |
| 17 | 27 | 2.6 | 1 | 1 | 0.5 | 0.5 | 1 | 0.5 | ≦.06 | ≦.06 |

TABLE II-continued

Antibacterial Activity, Minimal Inhibitory Concentration (MIC) against Various Organisms*

| 18 | 19   | 12   | 2  | 2  | 2  | 4  | 2  | 4  | 0.25  | 0.5   |
|----|------|------|----|----|----|----|----|----|-------|-------|
| 19 | 45   | 254  | 2  | 1  | 1  | 2  | 2  | 4  | 0.5   | 0.5   |
| 20 | 64   | 11   | 4  | 4  | 4  | 1  | 1  | 1  | ≦.06  | ≦.06  |
| 21 | >128 | 32   | 4  | 4  | 4  | 4  | 8  | 4  | ≦.06  | ≦.06  |
| 22 | 9.5  | 4.6  | 2  | 1  | 2  | 1  | 2  | 2  | ≦.06  | ≦.06  |
| 23 | 11   | 9.2  | 8  | 4  | 4  | 4  | 8  | 4  | 0.25  | 1     |
| 24 | >128 | >128 | 32 | 16 | 32 | 32 | 64 | 32 | 8     | 8     |
| 25 | 6.7  | 2.6  | 8  | 4  | 4  | 4  | 8  | 8  | 4     | 1     |
| 26 | 5.7  | 6.1  | 8  | 4  | 4  | 2  | 4  | 4  | 0.25  | ≦.06  |
| 27 | 9.5  | 6.1  | 64 | 32 | 32 | 8  | 32 | 8  | 64    | 32    |
| 28 | 6.7  | 7    | 8  | 8  | 8  | 4  | 2  | 4  | 4     | 16    |

| *ABBREVIATIONS | ORGANISM |
|---|---|
| RESISTANT | *Enterococcus faecium* and faecalis (geometric mean of 4–6 isolates) |
| SENSITIVE | *Enterococcus faecium* and faecalis (geometric mean of 4–6 isolates) |
| SA446 | *Staphylococcus aureus* 446 |
| SA489 | *Staphylococcus aureus* 489 |
| SA447 | *Staphylococcus aureus* 447 |
| SH 105 | *Staphylococcus haemolyticus* 105 |
| SH 415 | *Staphylococcus haemolyticus* 415 |
| SE 270 | *Staphylococcus epidermidis* 270 |
| SPY C203 | *Streptococcus pyogenes* C203 |
| SPN P1 | *Streptococcus pneumoniae* P1 |

We claim:

1. A compound of the formula

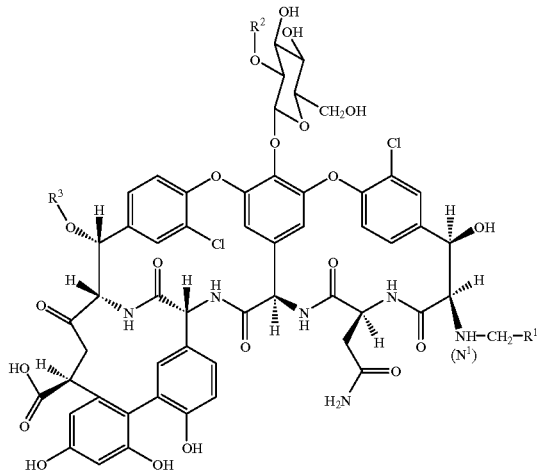

wherein $R^1$ represents alkyl of $C_1$–$C_{11}$, alkyl of $C_1$–$C_{11}$—$R^{1a}$, or $R^{1a}$-(linker$_{(0 \text{ or } 1)}$—$R^{1a}$)$_{0 \text{ or } 1}$, wherein each $R^{1a}$ is independently phenyl or phenyl substituted by one or two substituents, each of which is independently halo, hydroxy, loweralkyl of $C_1$–$C_8$, loweralkoxy of $C_1$–$C_8$, loweralkylthio of $C_1$–$C_4$, or trifluoromethyl, and "linker" is —O—, —CH$_2$—, or —O—(CH$_2$)$_n$— wherein n is 1-3; $R^2$ represents hydrogen or an epivancosaminyl radical of the formula

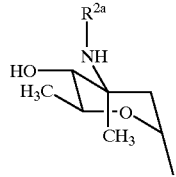

wherein $R^{2a}$ represents hydrogen or —CH$_2$—$R^1$ wherein $R^1$ is defined as above and may be the same or different than the $R^1$ on the $N^1$ position; and wherein $R^3$ represents an epivancosaminyl radical of the formula

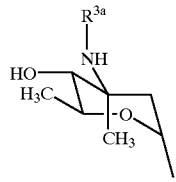

wherein $R^{3a}$ is hydrogen, or, when $R^2$ is an epivancosaminyl and $R^{2a}$ thereon is —CH$_2$—$R^1$, $R^{3a}$ can also represent —CH$_2$—$R^1$ identical to that on the $N^1$-position; or a pharmaceutically acceptable salt thereof.

2. A compound of claim 1 in which $R^1$ is $R^{1a}$—(linker$_{(0-1)}$—$R^{1a}$)$_{0 \text{ or } 1}$ as defined in claim 1.

3. A compound of claim 1 in which $R^2$ is an epivancosaminyl radical wherein $R^{2a}$ represents —CH$_2$—$R^1$.

4. A compound of claim 3 in which $R^{2a}$ is p-phenylbenzyl.

5. A compound of claim 3 in which $R^{2a}$ is p-(p-chlorophenyl)benzyl.

6. A process for the preparation of a compound as claimed in claim 1 which comprises reductively alkylating a parent glycopeptide of the formula

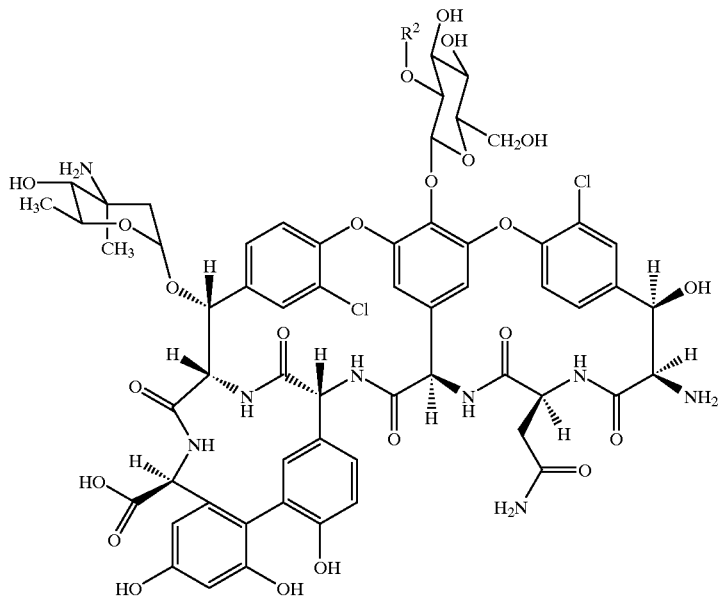

wherein $R^2$ is as defined in claim 1, with an aldehyde of the formula $R^1CHO$, wherein $R^1$ is as defined in claim 1.

7. The process of claim 6 further comprising the step of forming a pharmaceutically acceptable salt.

8. The process of claim 6 wherein said parent glycopeptide is prepared by (i) reacting an isothiocyanate of the formula $SCN-R^4$ with a compound having the formula

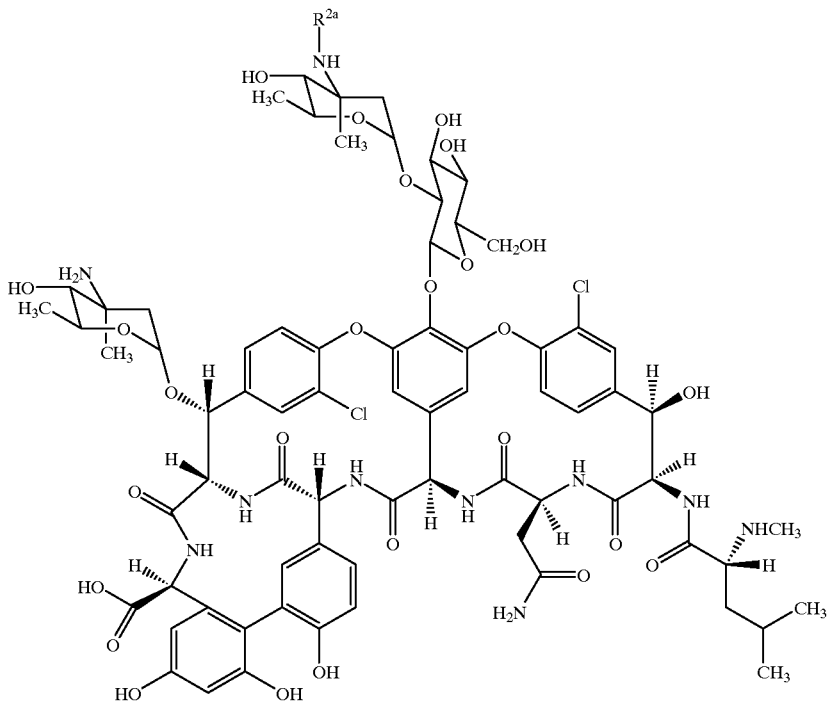

to obtain an intermediate $N^{LEU}$-(thiocarbamoyl)-A82846B compound of the formula

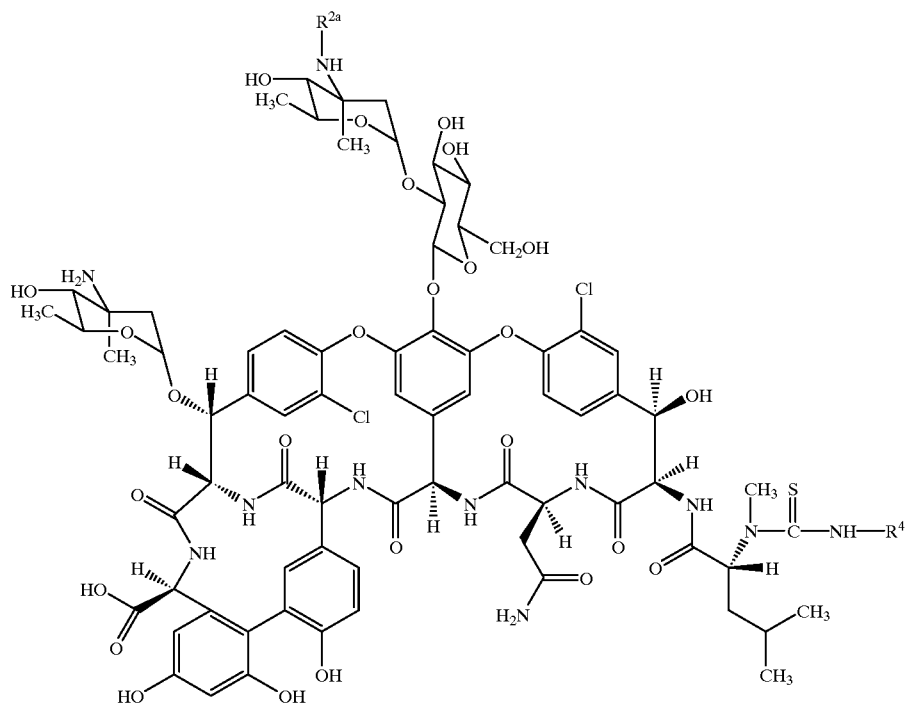

wherein, $R^4$ is alkyl of $C_1$–$C_{10}$, phenyl, naphthyl, or phenyl substituted by one or two substituents, each of which is independently halo, loweralkyl of $C_1$–$C_4$, loweralkoxy of $C_1$–$C_4$, benzyloxy, nitro, or

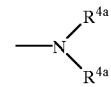

where each $R^{4a}$ is independently loweralkyl of $C_1$–$C_4$; and (ii) reacting said intermediate $N^{LEU}$-(thiocarbamoyl)-A82846B compound with an organic acid in a nonpolar solvent.

* * * * *